US012649739B2

(12) United States Patent
Simpson et al.

(10) Patent No.: US 12,649,739 B2
(45) Date of Patent: Jun. 9, 2026

(54) IMIDAZOQUINOLINE COMPOUND HAVING ANTI-INFLAMMATORY, ANTIFUGAL, ANTIPARASITIC, AND ANTICANCER ACTIVITY

(71) Applicant: PHARMA CINQ, LLC, Rockville, MD (US)

(72) Inventors: David Michael Simpson, North Bethesda, MD (US); Reid Warren Von Borstel, Potomac, MD (US); Rolando Alejandro Garcia Garcia, Germantown, MD (US)

(73) Assignee: PHARMA CINQ, LLC, Rockville, MD (US)

( * ) Notice: Subject to any disclaimer, the term of this patent is extended or adjusted under 35 U.S.C. 154(b) by 451 days.

(21) Appl. No.: 18/037,340

(22) PCT Filed: Dec. 9, 2021

(86) PCT No.: PCT/US2021/062565
§ 371 (c)(1),
(2) Date: May 17, 2023

(87) PCT Pub. No.: WO2022/125750
PCT Pub. Date: Jun. 16, 2022

(65) Prior Publication Data
US 2023/0416244 A1 Dec. 28, 2023

Related U.S. Application Data

(60) Provisional application No. 63/122,999, filed on Dec. 9, 2020.

(51) Int. Cl.

| | |
|---|---|
| ***C07D 471/04*** | (2006.01) |
| ***A61K 31/4745*** | (2006.01) |
| ***A61P 17/00*** | (2006.01) |
| ***A61P 35/00*** | (2006.01) |

(52) U.S. Cl.
CPC ............ *C07D 471/04* (2013.01); *A61P 17/00* (2018.01); *A61P 35/00* (2018.01)

(58) Field of Classification Search
CPC ................ C07D 471/06; C07D 471/04; A61K 31/4745; A61P 29/00; A61P 35/00
USPC ............................................ 546/82; 514/293
See application file for complete search history.

(56) References Cited

U.S. PATENT DOCUMENTS

| | | | |
|---|---|---|---|
| 3,541,094 A | 11/1970 | Lutz et al. | |
| 4,213,987 A | 7/1980 | Fujii et al. | |
| 4,323,680 A | 4/1982 | Nakagami et al. | |
| 4,331,667 A | 5/1982 | Schneider | |
| 4,689,338 A | 8/1987 | Gerster | |
| 4,698,348 A | 10/1987 | Gerster | |
| 4,940,714 A * | 7/1990 | Takada | A61P 25/26 546/82 |
| 5,114,939 A | 5/1992 | Dreikorn et al. | |
| 5,278,173 A | 1/1994 | Davis | |
| 5,294,622 A | 3/1994 | Dreikorn et al. | |
| 5,389,640 A | 2/1995 | Gerster et al. | |
| 5,770,599 A | 6/1998 | Gibson | |
| 6,046,206 A | 4/2000 | Pamukcu et al. | |
| 7,138,413 B1 | 11/2006 | Schwartz et al. | |
| 7,153,865 B2 | 12/2006 | D'Amico | |
| 7,176,213 B2 | 2/2007 | Aranyi et al. | |
| 7,365,089 B2 | 4/2008 | Aranyi et al. | |
| 7,419,977 B2 | 9/2008 | Aranyi et al. | |
| 7,470,709 B2 | 12/2008 | Barsanti et al. | |
| 7,572,915 B2 | 8/2009 | Barker et al. | |
| 7,875,624 B2 | 1/2011 | Heise et al. | |
| 7,928,111 B2 | 4/2011 | Tachdjian et al. | |
| 8,637,532 B2 | 1/2014 | Sutton et al. | |
| 10,030,015 B2 | 7/2018 | Simpson et al. | |
| 10,934,284 B2 | 3/2021 | Simpson et al. | |
| 2005/0131020 A1 | 6/2005 | D'Amico | |
| 2005/0137399 A1 | 6/2005 | Cai et al. | |
| 2006/0247223 A1 | 11/2006 | Schwartz et al. | |
| 2007/0105943 A1 | 5/2007 | Nakamoto et al. | |
| 2008/0213308 A1 | 9/2008 | Valiante et al. | |
| 2009/0163545 A1 | 6/2009 | Goldfarb | |
| 2009/0221556 A1 | 9/2009 | Kshirsagar et al. | |
| 2009/0311288 A1 | 12/2009 | Sutton et al. | |
| 2010/0120741 A1 | 5/2010 | Borchardt et al. | |
| 2010/0190808 A1 | 7/2010 | Mjalli et al. | |
| 2010/0331293 A1 | 12/2010 | Cushing et al. | |
| 2011/0092504 A1 | 4/2011 | Bo et al. | |
| 2012/0258975 A1 | 10/2012 | Yuan et al. | |
| 2018/0298000 A1 | 10/2018 | Simpson et al. | |
| 2021/0163476 A1 | 6/2021 | Simpson et al. | |

FOREIGN PATENT DOCUMENTS

| | | |
|---|---|---|
| AU | 2535384 A | 9/1984 |
| CN | 1034204 C | 3/1997 |
| CN | 1311678 A | 9/2001 |

(Continued)

OTHER PUBLICATIONS

International Search Report issued in PCT/US2021/062565, dated Feb. 23, 2022.

Gerster et al., "Synthesis and Structure-Activity-Relationships of 1H-Imidazo[4,5-c]quinolines That Induce Interferon Production," Journal of Medicinal Chemistry, vol. 48, pp. 3481-3491; 99. 3482 (2005).

PUBMED Compound Record for CID 14621819, "3H-Imidazo[4,5-c]quinoline, 2-(phenylmethyl)," U.S. National Library of Medicine, pp. 1-9, available at https://pubchem.ncbi.nlm.nih.gov/compound/14621819) (2007).

Adams et al., "Differences between central and peripheral rat alpha-adrenoceptors revealed using binuclear ligands," Eur. J. Pharmacol. 127: 27-35 (1986).

Alford et al., "Temporal infiltration of leukocyte subsets into mouse skin inflamed with phorbol ester," *Agents and Actions* 37:260-267 (1992).

(Continued)

*Primary Examiner* — Charanjit Aulakh
(74) *Attorney, Agent, or Firm* — MEDLER FERRO WOODHOUSE & MILLS PLLC

(57) ABSTRACT

An imidazoquinoline compound having activity against inflammation, fungi, unicellular parasitic microorganisms, and cancer is described.

12 Claims, 9 Drawing Sheets

(56) References Cited

FOREIGN PATENT DOCUMENTS

| | | | |
|---|---|---|---|
| DE | 3406992 | A1 | 9/1984 |
| EP | 0145340 | A2 | 6/1985 |
| EP | 0370704 | A2 | 5/1990 |
| EP | 0520722 | A1 | 12/1992 |
| EP | 0566226 | B1 | 11/1995 |
| EP | 0326331 | B1 | 4/2002 |
| GB | 1182507 | A | 2/1970 |
| GB | 1496371 | A | 12/1977 |
| GB | 2068732 | A | 8/1981 |
| GB | 2135887 | A | 9/1984 |
| JP | S43-20294 | Y1 | 8/1968 |
| JP | S53-103484 | A | 9/1978 |
| JP | S54-2325 | A | 1/1979 |
| JP | S55-76803 | A | 6/1980 |
| JP | H01-246266 | A | 10/1989 |
| JP | 2008-514548 | A | 5/2008 |
| JP | 2011-026251 | A | 2/2011 |
| KR | 2011-0121019 | A | 11/2011 |
| RU | 2248975 | C2 | 3/2005 |
| SU | 1111675 | A3 | 8/1984 |
| WO | 1990/000055 | A1 | 1/1990 |
| WO | 1992/015582 | A1 | 9/1992 |
| WO | 1996/009294 | A1 | 3/1996 |
| WO | 1997/048705 | A1 | 12/1997 |
| WO | 1998/022446 | A1 | 5/1998 |
| WO | 2005/033079 | A1 | 4/2005 |
| WO | 2006/034235 | A2 | 3/2006 |
| WO | 2006/071095 | A1 | 7/2006 |
| WO | 2007/056170 | A2 | 5/2007 |
| WO | 2007/075468 | A1 | 7/2007 |
| WO | 2010/074783 | A1 | 7/2010 |
| WO | 2011/060207 | A1 | 5/2011 |
| WO | 2012/079079 | A1 | 6/2012 |
| WO | 2012/149186 | A2 | 11/2012 |

OTHER PUBLICATIONS

Cantón et al., "Minimum fungicidal concentrations of amphotericin B for bloodstream *Candida* species," *Diagnostic Microbiology and Infectious Disease* 45(3):203-206 (2003).

Cavier et al., "Recherche sur les aminoquinoleines. XIX: Activite amoebicide in vivo d'alkylamino-4 quinoleines a longues chaines," Ann. Pharm. Fr. 36(3-4): 115-119 (1978). English Summary attached.

Chen et al., "[alpha]1-Adrenoceptor and serotonin 5-HT1A receptor affinity of homobivalent 4-aminoquinoline compounds: An investigation of the effect of linker length," Biochem. Pharmacol. 85(10): 1534-1541 (2013).

CLSI. *Reference Method for Broth Dilution Antifungal Susceptibility Testing of Yeasts; Approved Standard—Second Edition*. CLSI document M27-A2 (ISBN 1-56238-469-4). CLSI, 940 West Valley Road, Suite 1400, Wayne, PA 19087-1898 USA, 2002.

CLSI. *Reference Method for Broth Dilution Antifungal Susceptibility Testing of Filamentous Fungi; Approved Standard—Second Edition*. CLSI document M38-A2 [ISBN 1-56238-668-9]. CLSI, 940 West Valley Road, Suite 1400, Wayne, PA 19087-1898 USA, 2008.

Deshpande et al., "p-Toluenesulphonyl derivatives of N,N'-bis-(4-quinolino-4-quinaldino/4-quinazolino and 9-acridino) polymethylene diamines as hypoglycemic agents," J. Indian Chem. Soc. 52: 746-749 (1975).

Desvignes et al., "Recherche sur les aminoquinoleines. XVIII: Activite antibacterienne et antifongique in vitro d'alkylamino-4 quinoleines a longues chaines," Ann. Pharm. Fr. 35(7-8): 239-247 (1977). English Summary attached.

Ferguson et al., "The mutagenic effects of diacridines and diquinolines in microbial systems," Mutation Res. 232: 337-343 (1990).

Firestone et al., "Lysosomotropic agents. 7.1. Broad-spectrum antifungal activity of lysosomotropic detergents," J. Med. Chem. 30(8): 1519-1521 (1987).

Firestone, "Lysosomotropic agents. 1. Synthesis and cytotaxic action of lysosomotropic detergents," J. Med. Chem. 22(9): 1130-1133 (1979).

Galanakis et al., "Synthesis and quantitative structure-activity relationship of a novel series of small conductance Ca2+-activated K+ channel blockers related to dequalinium," J. Med. Chem. 39: 359-370 (1996).

Han et al., "Dual-site binding of bivalent 4-aminopyridine- and 4-aminoquinoline-based AChE inhibitors: contribution of the hydrophobic alkylene tether to monomer and dimer affinities," Bioorg. Med. Chem. 7: 2569-2575 (1999).

Harrison et al., "Conditional lethality of the diprotic weak bases chloroquine and quinacrine against Cryptococcus neoformans," *The Journal of Infectious Diseases* 182(1): 283-289 (2000).

Hocart et al., "4-Aminoquinolines active against chloroquine-resistant Plasmodium falciparum: Basis of antiparasite activity and quantitative structure-activity relationship analyses," Antimicrobial Agents and Chemother. 55(5): 2233-2244 (2011).

Ikeda et al., "Structure-activity relationship in the antitumor activity of 6-, 8- or 6,8-substituted 3-benzylamino-β-carboline derivatives." *Bioorganic & Medicinal Chemistry Letters* 22(10): 3506-3515 (2012).

Isham et al., "Voriconazole and Caspofungin Cidality Against Non-Albicans *Candida* Species. Infectious Diseases in Clinical Practice," 15(4):250-253 (2007).

Kovalenko et al., "Synthesis and Anticancer Activity of 2-(Alkyl-, Alkaryl-, Aryl-, Hetaryl-)- [1,2,4]triazolo[1,5-c]quinazolines," Sci. Pharm. 81(2): 359-391 (2013).

Li, Ping-ling, "Synthesis and evaluation of novel dimeric acetylcholinesterase inhibitors." Master Thesis, Hong Kong University of Science and Technology (1998). Available from Sel. Org. React. Database (SORD).

McAfee et al., "Autophagy inhibitor Lys05 has single-agent antitumor activity and reproduces the phenotype of a genetic authopagy deficiency," PNAS 109(21): 8253-8258 (2012).

McFadyen et al., "Alkyl-linked diquinolines are monofunctional AT-selective DNA-intercalating agents," FEBS Letters 228(2): 235-240 (1988).

McMahon, Gerald, "VEGF receptor signaling in tumor angiogenesis," The Oncologist 5(S1):3-10 (2000).

Miller et al., "Cell killing by lysosomotropic detergents," J. Cell. Biol. 97(6): 1841-1851 (1983).

Nadanaciva et al., "A high content screening assay for identifying lysosomotropic compounds," Toxicol. in Vitro 25(3): 715-723 (2011).

Nishimura et al., "Phosphoinositide 3-kinase (PI3K)/mammalian target of rapamycin (mTOR) dual inhibitors: discovery annd structure—activity relationships of a series of quinoline and quinoxaline derivatives," J. Med. Chem. 54(13): 4735-4751 (2011).

Pedersen et al., "Phosphoramides: XVI. Mixtures of phosphorous pentoxide, amine hydrochlorides and tertiary amines as reagents in the synthesis of quinolinamines," Chemica Scripta 18(5): 240-241 (1981).

Pinedo et al., "Translational research: the role of VEGF in tumor angiogenesis," The Oncologist, 5(S1):1-2 (2000).

Pivtoraiko et al., "Low-dose bafilomycin attenuates neuronal cell death associated with autophagy lysosome pathway dysfunction," Journal of Neurochemistry 114(4): 1193-1204 (2010).

Renault et al., "Aminoquinoleines secondaires a activite amoebicide potentielle: influence de la longueur et de la position de la chaine alkylaminee," C.R. Acad. Sc. Paris, Serie D, 282(5): 509-511; Feb. 1976. English Summary attached.

Renault et al., "Recherche sur les aminoquinoleines. I. Etude des diverses methodes de syntheses des amino-4 quinoleines secondaires et tertiares a chaines hydrocarbonees," Chimica Therapeutica 66(5-6): 339-346 (1966). English Summary on p. 346.

Srikanta et al., "A sensitive high-throughput assay for evaluating host-pathogen interactions in Cryptococcus neoformans infection," *PloS One* 6(7): e22773 (2011).

Sukhai et al., "Lysosomal disruption preferentially targets acute myeloid leukemia cells and progenitors," J. Clin. Investigation 123(1): 315-328 (2013).

(56) References Cited

OTHER PUBLICATIONS

Swindell et al., "Genome-wide expression profiling of five mouse models identifies similarities and differences with human psoriasis," PLoS One. 6(4):e18266 (2011).
Tomai et al., "Immunomodulating and antiviral activities of the imidazoquinoline S-28463," Antiviral Res. 28(3):253-264 (1995).
Van der Fits et al., "Imiquimod-induced psoriasis-like skin inflammation in mice is mediated via the IL-23/IL-17 axis," *Journal of Immunology* 182(9): 5836-5845 (2009).
Yap et al., "4-Arylalkoxyquinazolines with antifungal activity," Chapter 26, pp. 258-272 in "Synthesis and Chemistry of Agrochemicals V." Baker et al., eds. (ACS 1998).
Extended European Search Report issued in EP 14746786.4, dated Sep. 28, 2016.
Examination Report issued in AU 2014212242, dated Dec. 13, 2016.
CAS Registry No. 70137-87-0, STN Entry dated Nov. 16, 1984.
CAS Registry No. 70137-92-7, STN Entry dated Nov. 16, 1984.
CAS Registry No. 99011-37-7, STN Entry dated Nov. 9, 1985.
CAS Registry No. 100818-54-0, STN Entry dated Mar. 15, 1986.
CAS Registry No. 124532-49-6, STN Entry dated Jan. 5, 1990.
CAS Registry No. 130338-83-9, STN Entry dated Nov. 9, 1990.
CAS Registry No. 150450-55-8, STN Entry dated Oct. 7, 1993.
CAS Registry No. 477846-50-7, STN Entry dated Dec. 31, 2002.
CAS Registry No. 477861-85-1, STN Entry dated Dec. 31, 2002.
CAS Registry No. 477861-86-2, STN Entry dated Dec. 31, 2002.
CAS Registry No. 477861-94-2, STN Entry dated Dec. 31, 2002.
CAS Registry No. 512803-46-2, STN Entry dated May 9, 2003.
CAS Registry No. 512803-47-3, STN Entry dated May 9, 2003.
CAS Registry No. 512803-48-4, STN Entry dated May 9, 2003.
CAS Registry No. 853792-85-5, STN Entry dated Jul. 5, 2005.
CAS Registry No. 896727-22-3, STN Entry dated Jul. 28, 2006.
CAS Registry No. 896727-23-4, STN Entry dated Jul. 28, 2006.
CAS Registry No. 896727-24-5, STN Entry dated Jul. 28, 2006.
CAS Registry No. 896727-25-6, STN Entry dated Jul. 28, 2006.
CAS Registry No. 896727-26-7, STN Entry dated Jul. 28, 2006.
CAS Registry No. 896727-27-8, STN Entry dated Jul. 28, 2006.
CAS Registry No. 896727-28-9, STN Entry dated Jul. 28, 2006.
CAS Registry No. 926783-30-4, STN Entry dated Mar. 18, 2007.
CAS Registry No. 929371-13-1, STN Entry dated Apr. 8, 2007.
CAS Registry No. 929411-63-2, STN Entry dated Apr. 8, 2007.
CAS Registry No. 929411-69-8, STN Entry dated Apr. 8, 2007.
CAS Registry No. 1183483-77-3, STN Entry dated Sep. 13, 2009.
CAS Registry No. 1219551-40-2, STN Entry dated Apr. 19, 2010.
CAS Registry No. 1219574-88-5, STN Entry dated Apr. 19, 2010.
CAS Registry No. 1223418-83-4, STN Entry dated May 14, 2010.
CAS Registry No. 1262888-87-8, STN Entry dated Feb. 15, 2011.
CAS Registry No. 1262888-93-6, STN Entry dated Feb. 15, 2011.
CAS Registry No. 1262888-99-2, STN Entry dated Feb. 15, 2011.
CAS Registry No. 1289188-18-6, STN Entry dated May 3, 2011.
CAS Registry No. 1291543-40-2, STN Entry dated May 8, 2011.
CAS Registry No. 1305730-10-2, STN Entry dated Jun. 5, 2011.
CAS Registry No. 1306986-04-8, STN Entry dated Jun. 7, 2011.
CAS Registry No. 1320982-96-4, STN Entry dated Aug. 21, 2011.
CAS Registry No. 1327861-54-0, STN Entry dated Sep. 4, 2011.
CAS Registry No. 1327861-60-8, STN Entry dated Sep. 4, 2011.
CAS Registry No. 1327861-77-7, STN Entry dated Sep. 4, 2011.
CAS Registry No. 1327947-30-7, STN Entry dated Sep. 4, 2011.
CAS Registry No. 1328271-44-8, STN Entry dated Sep. 5, 2011.
CAS Registry No. 1328292-16-5, STN Entry dated Sep. 5, 2011.
CAS Registry No. 1328808-73-6, STN Entry dated Sep. 6, 2011.
CAS Registry No. 1329224-28-3, STN Entry dated Sep. 7, 2011.
CAS Registry No. 1329267-61-9, STN Entry dated Sep. 7, 2011.
CAS Registry No. 1350730-84-5, STN Entry dated Dec. 13, 2011.
RN384374-55-4, STN Registry, Jan. 19, 2002.
RN1027641-33-3, STN Registry, Jun. 12, 2008.
RN1292730-81-4, STN Registry, May 10, 2011.
RN1303776-05-7, STN Registry, Jun. 1, 2011.
RN1304938-90-6, STN Registry, Jun. 3, 2011.
RN1305730-07-7, STN Registry, Jun. 5, 2011.
RN1305730-17-9, STN Registry, Jun. 5, 2011.
RN1305730-33-9, STN Registry, Jun. 5, 2011.
STN Registry No. 1621343-19-8, 2014.
STN Registry No. 1621343-21-2, 2014.
Iwakura et al., "The IL-23/IL-17 axis in inflammation," *The Journal of Clinical Investigation* 116(5): 1218-1222 (2006).
Wang, "Synthesis of 2H-indazole and benzimidazole derivatives based on radical reaction," *Wanfang Data Platform* 1-100 (2021), English Machine Translation of Abstract.

* cited by examiner

IMIDAZOQUINOLINE COMPOUND HAVING ANTI-INFLAMMATORY, ANTIFUGAL, ANTIPARASITIC, AND ANTICANCER ACTIVITY

BACKGROUND OF THE INVENTION

Most nucleated eukaryotic cells, whether unicellular organisms or constituents of multicellular organism including humans, contain acidified vacuoles that are critical for cellular maintenance and function. In mammalian cells, these vacuoles comprise lysosomes and other endosomal vesicular organelles. The pH of the interior of lysosomes is typically about 4.5 to 5, maintained by vacuolar ATP-dependent proton pumps and also by Donnan equilibrium effects. Lysosomes contribute to cytosolic pH buffering, protecting the cell from acidic environments, and are also primary sites for degrading and recycling the constituents of aging or damaged organelles such as mitochondria, a process known as autophagy. There are several important pathological conditions where lysosomal characteristics are altered and contribute to disease pathogenesis, presenting a potential target for pharmacological therapy.

A growing body of evidence indicates that a common phenotypic change in invasive cancer cells is a redirection of lysosomes to participate in destruction of surrounding cells via exocytosis of acidic contents, including enzymes. Proteolytic enzymes normally found in lysosomes but secreted by cancer cells, such as cathepsins, can degrade extracellular matrix proteins, facilitating tumor invasion and metastasis. Furthermore, lysosomes and other acidic vacuolar organelles are often enlarged in cancer cells, which aids pH buffering; many solid tumors generate an acidic extracellular environment, favoring invasion, which requires that cancer cells adapt to both produce and tolerate a low extracellular pH. Cancer cells selected in vitro for invasive potential have larger, more acidic lysosomes than do less aggressive cells. Cancer cells exposed to ionizing radiation undergo a protective response involving enlargement and acidification of lysosomes. A related protective response through which cancer cells acquire survival advantages is activation of autophagy. Activation of autophagy involves fusion of autophagosomes containing damaged organelles or other cell debris with lysosomes; disruption of autophagy can impair cancer cell viability. Some cancer cells also sequester chemotherapy agents in lysosomes as a mechanism of drug resistance. Chloroquine, an antimalarial drug that accumulates in mammalian lysosomes, potentiates, or restores sensitivity to, anticancer activity of several classes of chemotherapy agents and targeted small molecule and antibody cancer treatments. Lysosomotropic fluorescent dyes such as acridine orange can be used to visually differentiate tumors in situ from surrounding tissues, indicating a potential sharp distinction for specific lysosome-targeting cytotoxic agents to selectively kill cancer cells.

Lysosomal alterations are also important features of common inflammatory diseases, especially those involving activated macrophages, where exocytosis of lysosomal enzymes, cytokines, and some inflammatory mediators such as HMBG1 that are processed and released via lysosomes, can participate in tissue damage and both local and systemic inflammation. Glucocorticoid signaling is also linked to lysosomes, such that compromising lysosomal function can enhance anti-inflammatory pathways mediating glucocorticoid effects.

Most fungi have acidic vacuoles similar to lysosomes. These acidic vacuoles are critical for ion and pH homeostasis, storage of amino acids, autophagy and for processing some proteins. Vacuoles are acidified via a proton pump, the vacuolar $H^+$-ATPase, or "V-ATPase", and it is known that fungi with inactivating mutations of subunits of V-ATPase that result in impaired vacuole acidification also lose virulence and grow poorly. Ergosterol, a steroid which is a major and specific membrane component of fungal membranes, is critical for conformation and activity of the V-ATPase, and V-ATPase dysfunction appears to be a major mechanism of antifungal activity of ergosterol synthesis inhibitors, which includes several classes of existing antifungal agents. Antifungal agents that act via binding to specific proteins, e.g. enzyme inhibitors, are inherently vulnerable to development of drug resistance via single mutations in genes encoding target proteins. Agents that target fungi via adequately specific targeting and disruption of fungal acidic vacuoles by cation trapping may be less susceptible to development of resistance through point mutations than are drugs acting by binding to specific protein targets, due to impaired viability and virulence when vacuolar acidification is impaired.

Clinically important antimalarial drugs are known that accumulate in acidic vacuoles and lysosomes, and their biological activity is largely mediated through their concentration in acidic vacuoles, not only in malaria but in inflammatory diseases, some cancers, and non-malarial infections by fungi and unicellular and protozoal parasites. Quinoline analog antimalarial drugs target malaria plasmodia via cation trapping in acidic digestive vacuoles, where they can accumulate to concentrations several orders of magnitude higher than in extracellular spaces. A large molar fraction of chloroquine, mefloquine, quinacrine, and several of their congeners are uncharged at the usual extracellular pH of about 7.4 and the cytoplasmic pH of 7.1, and can thereby pass through cellular and organelle membranes. In an acidic environment, such as the interior of a lysosome or fungal acidic vacuole, these antimalarials are predominantly cationic and are thereby restricted from free passage through the vacuolar membrane. Antimalarials such as chloroquine impair processing of heme from hemoglobin ingested by malaria plasmodia after accumulating in the feeding vacuoles, accounting for much of their specific toxicity to plasmodia. However, chloroquine and similar quinoline-analog antimalarials can accumulate in mammalian lysosomes and fungal acidic vacuoles and impair vacuolar function to a degree sufficient to provide some clinical benefit, if only by partially deacidifying the vacuoles. Chloroquine is used for treatment of chronic autoimmune and inflammatory diseases such as systemic lupus erythematosis or rheumatoid arthritis, with moderate efficacy. A degree of antifungal activity has been reported for antimalarials such as chloroquine or quinacrine, both as single agents or in combination with other classes of antifungal agents, such as fluconazole, notably in animal models of systemic cryptococcosis. However, their activity is suboptimal, yielding incomplete fungal growth inhibition. Recent work has also demonstrated moderate growth inhibitory activity of chloroquine, mefloquine, and other weakly cationic drugs such as siramesine in animal models of cancer. Existing lysosomotropic agents such as antimalarial quinoline compounds can thus display some therapeutically relevant activity in diseases in which acidic vacuoles contribute to pathogenesis. However, the activity and potency of antimalarials in such diseases are limited, as the target cells can tolerate accumulation of relatively high concentrations of the antimalarials (the specific lethal effect of quinoline compounds in malaria is largely attributed to disruption of heme processing within plasmodial feeding vacuoles, a mechanism of cytotoxicity not applicable in the areas of inflammatory disease, cancer, or fungal infections). Despite the body of evidence indicating strong potential for targeting lysosomes for treating cancers, existing agents have not shown adequate activity or therapeutic index for effectively treating cancer in humans.

"Lysosomotropic detergents", comprising weakly cationic heterocyclic moieties bearing a single alkyl chain with approximately 10 to 14 carbon atoms, were reported to be potently cytotoxic to mammalian cells and to display broad spectrum antifungal activity in vitro. This class of agents accumulate in lysosomes and acidic vacuoles via the same type of cation trapping process through which antimalarials are concentrated, and when they reach a critical micellar concentration in the vacuole, they behave as detergents, damaging vacuolar membranes. They display a characteristic sigmoid dose-response curve as a consequence of their formation of micellar micro structures. However, there is no information about activity or safety of this class of agents in vivo in animal models of relevant diseases.

SUMMARY OF THE INVENTION

This invention provides the following compound: 2-(3-Phenoxybenzyl)-1H-imidazo[4,5-c]quinoline and pharmaceutically acceptable salts thereof.

This invention also provides a use or method for treating or preventing a condition in a mammalian subject; the condition being selected from the group consisting of an inflammatory disease, a fungal infection, a unicellular parasitic infection, and a neoplastic disease; comprising administering to the subject an effective amount of the compound or salt of the invention. It also provides compositions comprising this compound or its salts. And it provides a method of inhibiting a fungus ex vivo, comprising contacting a surface or the fungus with the compound or salt.

DETAILED DESCRIPTION OF THE INVENTION

Figure 1:
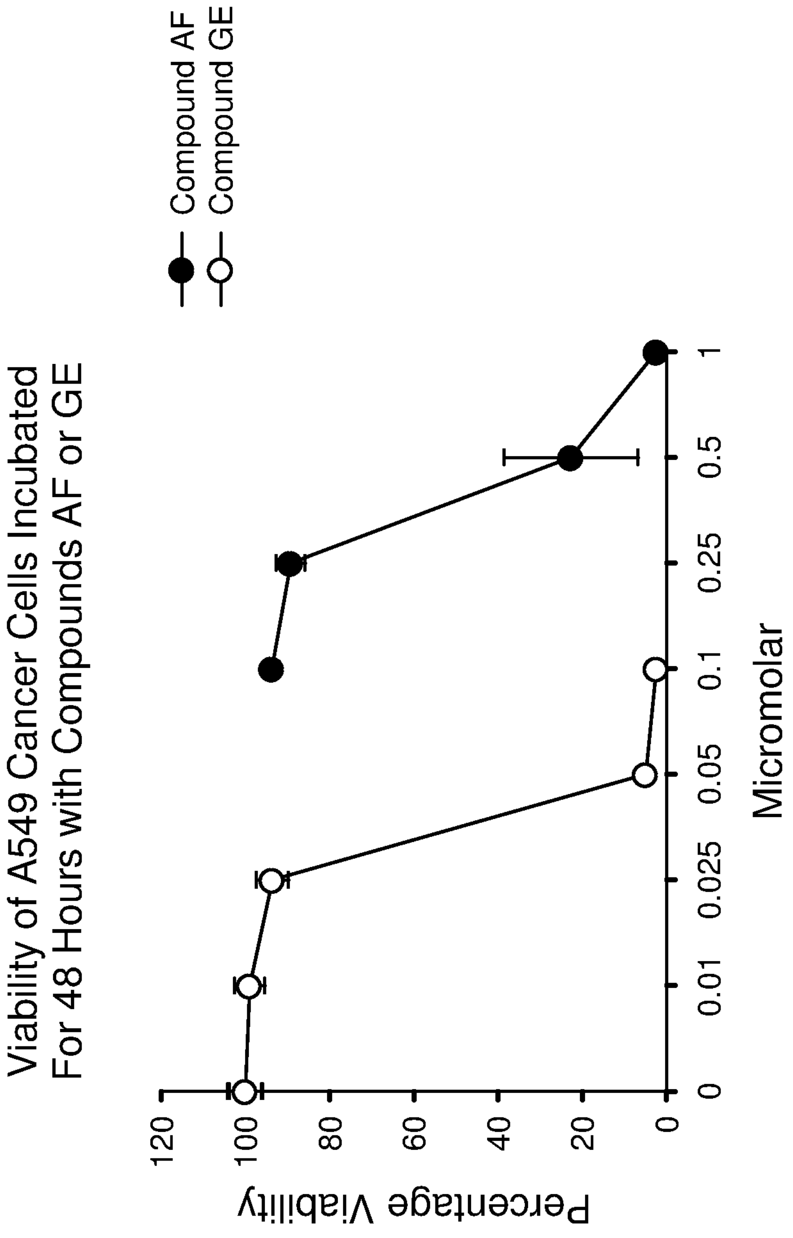
FIG. 1: Viability of A549 Cancer Cells Incubated for 48 Hours with Compounds AF or GE
Figure 2:
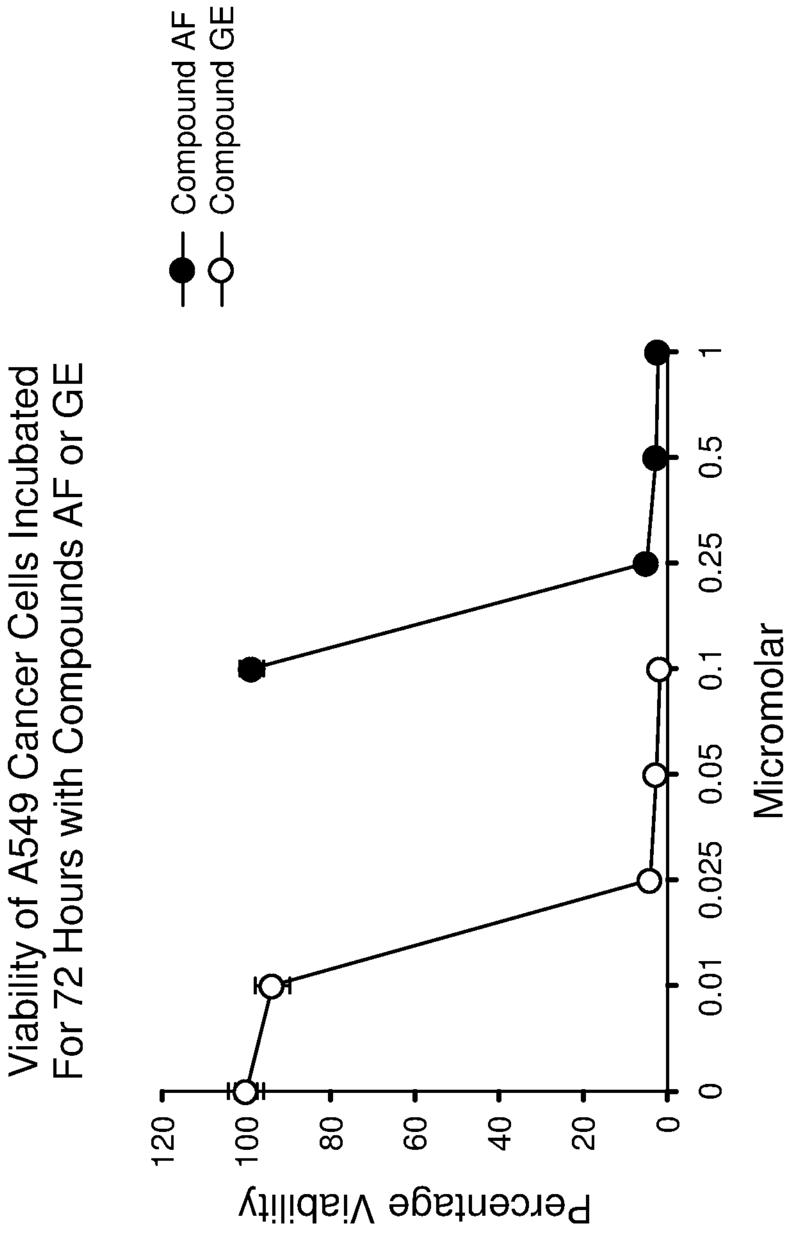
FIG. 2: Viability of A549 Cancer Cells Incubated for 72 Hours with Compounds AF or GE

Without wishing to be bound by theory, this invention provides compounds and their use for treating diseases characterized by pathogenic cells featuring lysosomes or other acidic vacuoles with disease-related alterations predisposing them to accumulation of compounds of the invention, which then selectively inactivate or eliminate such pathogenic cells. Compounds of the invention feature significant improvements in potency and activity over known aminoquinoline drugs such as chloroquine, as a consequence of structural moieties that potently disrupt lysosomal or vacuolar membrane integrity when the compounds accumulate in acidic vacuoles in cells. Diseases that are at least moderately responsive to antimalarial quinoline derivatives and analogs, are in general more effectively treated with compounds of the invention. Such diseases broadly comprise inflammatory diseases, neoplastic diseases, including both hematologic cancers and solid tumors, and infections by eukaryotic pathogens, including fungi and several classes of protozoal or other unicellular parasites.

Definitions

Certain chemical compounds are referred to herein by their chemical name or by the two-letter code shown below. Compound GE is a compound of this invention. Compound AF is disclosed in WO2014/120995 A2 (Wellstat Therapeutics Corp.).

GE 2-(3-Phenoxybenzyl)-1H-imidazo[4,5-c]quinoline

AF N-(3-Phenoxybenzyl)quinolin-4-amine

As used herein the transitional term "comprising" is open-ended. A claim utilizing this term can contain elements in addition to those recited in such claim.

The following abbreviations are used in the chemical synthesis examples and elsewhere in this description:

DCM dichloromethane

DMAP 4-(N,N-dimethylamino)pyridine

DMF N,N-dimethylformamide

EDC 1-ethyl-3-(3-dimethylaminopropyl)carbodiimide) hydrochloride

EtOH ethanol

EtOAc ethyl acetate

MeOH methanol

TEA triethylamine

TFA trifluoroacetic acid

TLC thin layer chromatography

Uses and Methods of Treatment

This invention provides certain compounds, described below, for treating diseases characterized by pathogenic cells featuring lysosomes or other acidic vacuoles with disease-related alterations predisposing them to accumulation of compounds of the invention, which then selectively inactivate or eliminate such pathogenic cells. Compounds of the invention feature significant improvements in potency and activity over known aminoquinoline drugs such as chloroquine, as a consequence of structural moieties that potently disrupt lysosomal or vacuolar membrane integrity when the compounds accumulate in acidic vacuoles in cells. Diseases that are at least moderately responsive to antimalarial quinoline derivatives and analogs are in general more effectively treated with compounds of the invention. Such diseases broadly comprise inflammatory diseases, neoplastic diseases, including both hematologic cancers and solid tumors, and infections by eukaryotic pathogens, including fungi and several classes of protozoal or other unicellular parasites.

Anti-Inflammatory Use

An important action of compounds of the invention is anti-inflammatory activity, providing utility for treating or preventing diseases or symptoms related to excessive tissue inflammation. This invention also provides compositions containing a compound of this invention as well as the use of a compound of this invention for the manufacture of a medicament for treatment or prevention of inflammatory diseases. Compounds of the invention selectively suppress or inactivate macrophages that have been stimulated into a pro-inflammatory state, with less of an effect on non-stimulated macrophages. Activated pro-inflammatory macrophages contribute to pathogenesis of a large variety of inflammatory and autoimmune diseases. Macrophages are both antigen presenting cells and effectors for tissue damage directed by autoreactive T cells, and participate in tissue damage and dysfunction in diseases including but not limited to rheumatoid arthritis, systemic lupus erythematosis, psoriasis, inflammatory bowel disease, and atopic dermatitis. Inflammatory macrophages participate in many systemic diseases, including autoimmune diseases, cardiovascular and metabolic diseases, and neurodegenerative conditions. Activated macrophages play a primary role in tissue damage involving instability of atherosclerotic plaques, with consequent risk of rupture and thrombotic vessel occlusion. Activated macrophages in adipose tissue contribute to metabolic abnormalities including insulin resistance, type 2 diabetes, and other consequences of obesity. Osteoclasts are macrophage-like cells that mediate bone degeneration in osteoporosis and participate in bone destruction and "bone pain" in cancers arising in or metastasized to bones. Compositions of the invention are useful for treating these and other disorders in which activated macrophages contribute to inflammatory disease pathogenesis.

Several classes of topical agents are used for treatment of inflammatory diseases of the skin, such as atopic dermatitis, eczema, or psoriasis. Corticosteroids are widely used, but have the potential for both local and systemic toxicities, particularly with prolonged use. They can cause local skin atrophy or thinning, which may lead to disruption of the skin, as well as telangiectasia. Furthermore, topical corticosteroids can be absorbed systemically in amounts sufficient to cause systemic side effects. A second class of agents for treatment of atopic dermatitis is T cell immunosuppressants, such as the calcineurin inhibitors tacrolimus and pimecrolimus. Their local and systemic immunosuppressive effects have led to concerns about depressing immunosurveillance of cancers, including melanomas and lymphomas.

Vitamin D analogs, notably calcipotriene, are known for topical treatment of psoriasis. Calciptoriene acts by inhibiting excessive proliferation of keratinocytes. Application to normal skin is contra-indicated due to a bleaching effect, and there is also a possibility of adverse events from systemic absorption. Dermal irritation or itching is a known side effect of calcipotriene. Compounds of the invention are particularly active against macrophage precursors that have been activated by exposure to vitamin D3. It is possible that psoriasis treatment with calcipotriene, while providing some improvements by inhibiting keratinocyte proliferation, may also direct local macrophages toward a pro-inflammatory state, contributing to known side effects such as irritation, and limiting the net therapeutic effect. In view of the ability of compounds of the invention to inactivate pro-inflammatory vitamin D3-primed macrophage precursors, combination topical treatment with compounds of the invention and vitamin D analogs may provide unexpected benefits in psoriasis and psoriatic dermatitis, both in treating the inflammatory epidermal hyperproliferation and in reducing irritation or itching as side effects of vitamin D analogs.

Compounds of the invention are useful for treating ocular inflammation, including keratitis, whether caused by infection (fungal, bacterial, amoebic) or by non-infectious triggers such as corneal injury or contact lenses. Compounds of the invention are especially suitable for fungal keratitis, counteracting both infectious fungi and concurrent inflammatory damage. Compounds of the invention inhibit corneal angiogenesis and other inflammatory changes in response to mechanical or chemical injury.

Compounds of the invention are useful for treating a variety of inflammatory or hyperproliferative skin conditions or lesions, including but not limited to eczema, atopic dermatitis, psoriasis, and impetigo. Impetigo is a superficial bacterial skin infection with inflammatory damage to the epidermia; compounds of the invention both suppress inflammation and have direct inhibitory or bactericidal effects on gram positive bacteria, including but not limited to *Staphylococcus aureus* and *Staphylococcus pyogenes*, the primary organisms responsible for impetigo. Compounds of the invention also inhibit pre-neoplastic and neoplastic skin alterations, which often exhibit characteristics of both inflammation and neoplasia, including but not limited to actinic keratosis, seborrheic keratoses, and warts.

Macrophages and related cell types contribute to pathogenesis of autoimmune diseases involving the adaptive immune system both as antigen presenting cells and as effectors damaging tissues after inappropriate stimulation by T cells, which secrete interferon gamma and other inflammatory mediators that recruit and activate macrophages. Compounds of the invention disrupt antigen presentation by macrophages and dendritic cells, and also inactivate pro-inflammatory effector macrophages that damage tissues. A general guidance is that compounds of the invention are useful for treating chronic or episodic autoimmune diseases where chloroquine, hydroxychloroquine or other antimalarial quinoline analogs display activity in humans or relevant animal models, and are generally more potent and active than the antimalarials in inflammatory and non-malaria infectious diseases. Such diseases include but are not limited to rheumatoid arthritis, systemic and discoid lupus erythematosis, psoriatic arthritis, vasculitis, Sjogrens syndrome, scleroderma, autoimmune hepatitis, and multiple sclerosis.

Macrophage activation syndrome (MAS) is an acute complication of several autoimmune diseases, especially in childhood-onset conditions such as idiopathic juvenile arthritis where it affects more than 10% of patients, and also in inflammatory bowel diseases. In MAS, macrophages are over-activated, causing damage to the hematopoietic system and systemic inflammation; MAS is sometimes lethal. Compounds of the invention are useful for treatment of MAS, and are optionally delivered orally or by intravenous injection or infusion.

For treatment of chronic autoimmune disorders, compounds of the invention are administered systemically, preferably orally. For treatment of acute inflammatory conditions, or flares of autoimmune diseases, intravenous treatment with compounds of the invention is an optional suitable delivery route.

For oral or intravenous treatment of autoimmune or inflammatory diseases, compounds of the invention are typically administered in doses ranging from 1 to 1000 milligrams per day, advantageously 100 to 600 milligrams per day, in single doses or divided into two or three doses per day.

Antifungal and Antiparasitic Uses

The compounds of this invention are useful in inhibiting fungal growth, both in vivo and ex vivo. Accordingly this invention also provides methods and uses for inhibiting the growth of a fungus in a mammalian subject, for example a human. These methods can be used to treat and to prevent fungal infection. Ex vivo, it is useful to treat surfaces with a compound of this invention to inhibit or prevent fungal growth, or in agriculture or horticulture to prevent or treat fungi that affect valuable plants. This invention also provides compositions containing a compound of this invention as well as the use of a compound of this invention for the manufacture of a medicament for inhibiting the growth of a fungus.

This invention is based, in part, on the finding that the compounds of this invention are effective in inhibiting the growth of a variety of fungal species, as shown in the biological activity examples below. Without wishing to be bound by theory, it is believed that compounds of this disclosure exploit the vulnerability of the fungal acidic vacuole. They are believed to accumulate in acidic vacuoles via cation trapping, and furthermore exert antifungal activity by disrupting the structure and function of the acidic vacuoles.

In accordance with this invention, the growth of fungi generally is inhibited. Examples of fungi that can be inhibited include but are not limited to *Candida, Saccharomyces, Trichophyton, Cryptococcus, Aspergillus*, and *Rhizopus*. In more specific embodiments of this invention the fungus is *Candida albicans; Candida glabrata; Saccharomyces cerevisiae; Trichophyton rubrurn; Cryptococcus neoformans*, for example *Cryptococcus neoformans* serotypes D and A; and *Aspergillus fumigatus*.

This invention also provides methods of treating and preventing parasitic infections. Due to the capability of compounds of the invention to enter and accumulate within acidic vacuoles in cells, they are useful for treating infections due to parasitic microorganisms that reside within acidic vacuoles in macrophages and other cell types. Tuberculosis (mycobacteria), listeria or *Staphylococcus* (gram positive bacteria), *Cryptococcus* (fungus), and leishmania and trypanosomes (amoebae), *Coxiella burnetii* (gram negative bacteria), and *Plasmodium* (some of which cause malaria) are nonlimiting examples of important such infectious organisms, in which residence within macrophages can protect the organisms from cellular or humoral immunity, or reduce the efficacy of drug treatments.

Compounds of the invention, which bear lipophilic moieties and are generally partially neutral at physiological pH (7.3), can pass freely into acidic vacuoles harboring parasites, and are concentrated and trapped there due to ionization in the acidic environment (pH 4-6.5). These compounds disrupt the structure and function of acidic vacuoles as hospitable sites for parasites and also have direct antiparasitic activity, due to acidic vacuoles within many parasitic organisms.

Parasites whose viability or virulence is dependent on integrity and function of an acidic vacuole are also vulnerable to compounds of the invention, similar to the basis for their antifungal activity. The acidic vacuole of malaria plasmodia provides an environment for concentration of compounds of the invention. Similarly, trypanosomes have a large acidic vacuole which is necessary for utilization of environmental nutrients. Compounds of the invention are useful for treatment or prevention of malaria and trypanosome infections. More broadly, protozoal parasites in general use acidified digestive vacuoles for acquisition and digestion of food, and are therefore susceptible to antiparasitic actions of compounds of the invention.

The antimalarial drug chloroquine is reported to have antiparasitic activity against a variety of organisms harbored in acidic vacuoles in host cells, or which have acidic vacuoles themselves, including but not limited to tuberculosis mycobacteria, cryptosporidium, leishmania and cryptococcus. In general, chloroquine acts by accumulating in acidic vacuoles via cation trapping. Activity of chloroquine is thus an indicator of likely activity of compounds of the inventions, with the difference that compounds of the invention are substantially more potent and active than is chloroquine. Chloroquine, despite published reports showing that it can improve survival in animal models of cryptococcosis, displays a ceiling of about 40% inhibition of *C. neoformans* growth in vitro, whereas compounds of the invention are substantially more potent than chloroquine and can cause 100% inhibition of *Cryptococcus* growth, due to superior disruption of the membranes of acidic vacuoles in which the respective drugs are accumulated.

For treatment of fungal or parasitic infections, compounds of the invention are administered in vehicles and by routes of administration appropriate for the nature and location of the infection. For dermal or nail infections, compounds of the invention are applied in a topical formulation which is optionally a lotion, ointment, solution, suspension, or spray. For ocular fungal infections, compounds of the invention are formulated in eyedrops. For systemic infections, compounds of the invention are administered orally in tablets, capsules, dragees, solutions or suspensions, or administered systemically by injection in saline, lipid emulsions, liposomes or other standard parenteral vehicles. Lung infections, especially involving organisms residing alveolar macrophages, are optionally treated via inhalational delivery of compounds of the invention and suitable excipients known to be acceptable for inhalational drug delivery. For intravenous or oral administration to treat systemic infections, compound of the invention are administered in doses ranging from 10 to 2000 milligrams per day, advantageously 200 to 1000 milligrams per day.

Other classes of antifungal agents in clinical use include inhibitors of ergosterol synthesis ("azole" antifungals including but not limited to fluconazole, ketoconazole, voriconazole, and allylamines including but not limited to terbinafine), polyene antifungals which act by binding to fungal membrane constituents, especially ergosterol (including but not limited to amphotericin B or nystatin), echinocandin inhibitors of glucan synthesis (including but not limited to caspofungin), and other agents known as active antifungals in medical practice. Compounds of the invention act via a distinct mechanism of action versus existing clinically important antifungals and are optionally coadministered with one or more other antifungal agent to improve overall antifungal treatment. Compounds of the invention are coadministered as separate pharmaceutical formulations, or are optionally formulated into a single combined-drug product. A combination of compounds of the inventions with azole antifungals is particularly advantageous as a completely oral regimen for use against cyptoccoccosis, which otherwise generally requires amphotericin B injections or infusions for initial induction. Compounds of the invention are also optionally coadministered with amphotericin B. One formulation of amphotericin B involves its incorporation into lipids comprising the membranes of liposomes. Because many of the compounds of the invention bear lipophilic moieties that insert into lipid membranes, they are advantageously incorporated into liposomes, either as single agents or in combination with amphotericin B or other known polyene antifungal agents.

Anticancer Uses

This invention provides compounds that are useful for systemic treatment of cancer based on consistent lysosomal changes characterizing invasive cancers. Lysosomal changes in cancer, including their enlargement and acidification, facilitates survival of cancer cells in acidic extracellular environments, and also increases the ability of cancer cells to invade surrounding tissues, through exocytosis of lysosomal contents, including proteases and polysaccharidases which can degrade extracellular matrix components. However, these stereotyped changes in lysosomal properties can render cancer cells vulnerable to lysosome-disrupting agents with appropriate physicochemical properties for selectively accumulating in and damaging lysosomes in cancer cells versus normal tissues.

Compounds of the invention accumulate in lysosomes in cancer cells and disrupt their integrity, thereby displaying potent selective cytotoxic activity against cancer cells in vivo and in vitro.

Because one major mechanism for cancer cell resistance to a variety of chemotherapy agents is to sequester them in lysosomes and other acidic vesicular compartments, compounds of the invention are able to restore or enhance sensitivity of cancer cells to a variety of classes of anticancer agents, including antimetabolites, tyrosine kinase inhibitors, anticancer antibodies against growth factor receptors, anthracyclines, platinum compounds, alkylating agents, and antibodies. Compounds of the invention typically do not display toxicities overlapping dose limiting toxicities of most anticancer agents, permitting combination of compounds of the invention with other classes of antineoplastic drugs with a net improvement in efficacy and therapeutic index.

Cancer cells exposed to sublethal doses of ionizing radiation undergo a protective response that increases their resistance to subsequent irradiation. A component of this protective response is formation of enlarged lysosomes or other acidified vacuolar organelles; inhibition of the vacuolar ATPase responsible for acidifying lysosomes with bafilomycin A prevents the protective response in sublethally irradiated cells and sensitizes cancer cells to ionizing radiation. Lysosomal damage is a significant mediator of radiation-induced death in cancer cells. By disrupting the integrity of lysosomal membranes, compounds of the invention are useful for reducing resistance of cancer cells to therapeutic ionizing radiation and for potentiating anticancer effectiveness of ionizing radiation therapy. Compounds of the invention are optionally administered prior to ionizing radiation therapy of cancer (whether with external irradiation or administration of antibody-targeted radioisotopes) as radiosensitizers, or they may be given after irradiation to attack surviving cancer cells undergoing protective responses to nonlethal irradiation involving production or enlargement of acidic vacuoles.

One mechanism imparting selective survival and proliferation advantages in some cancers is upregulation of autophagy, a process through which damaged organelles or other cell debris are engulfed by autophagosomes, which fuse with lysosomes to digest and recycle constituent molecules. By concentrating in and disrupting lysosomes, compounds of the invention impair autophagy in cancer cells, thereby reducing their viability and resistance to other anticancer treatments.

For treatment of cancer, compounds of the invention are administered by oral or intravenous administration in doses of 10 to 2000 milligrams per day. Compounds of the invention are administered as single agents or in combination with other cancer treatments appropriate for a particular type of cancer, and generally in doses when such agents are used alone, as compounds of the invention will generally not have overlapping toxicities with other classes of anticancer agents that would necessitate substantial dose reduction.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 10 to 1000 mg of the compound of this invention. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees, and hard gelatin capsules. Suitable carriers for soft gelatin capsules are, for example, vegetable oils, waxes, fats, semi-solid and liquid polyols, and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils, and the like. Suitable carriers for suppositories are, for example, natural or hardened oils, waxes, fats, semi-liquid or liquid polyols, and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents, or antioxidants. They can also contain still other therapeutically valuable substances, particularly anti-inflammatory or antifungal agents (depending on whether an inflammatory disease or a fungal infection or cancer are being addressed in a patient) that act through mechanisms other than those underlying the effects of the compounds of the invention.

For treatment of cancer, preferred additional drugs that can advantageously be coadministered or coformulated with a compound of the invention comprise orally active anticancer agents. Because compounds of the invention act through a unique mechanism not shared by other anticancer drugs, they are compatible with a large variety of concurrent therapies, including antimetabolites, anthracyclines, tyrosine kinase inhibitors, platinum drugs, or alkylating agents. Such agents, when orally active, are administered or coformulated to deliver quantities of drugs determined in previous clinical trials to be effective and adequately tolerated.

For systemic treatment of diseases, including some cancers, inflammatory conditions and fungal or protozoal infections, compounds of the invention are optionally administered by intravenous injection or infusion. For intravenous administration, compounds of the invention are dissolved in suitable intravenous formulations as solutions or in lipid emulsions, using standard excipients known in the art as well-tolerated intravenous formulation ingredients and compositions. Suitable volumes and concentrations are selected for delivery of 10 to 2000 milligrams of compounds of the invention per day, depending on the specific requirements for a compound, and a disease condition as determined in clinical trials.

Compounds of the invention are optionally incorporated into liposomal formulations. The lipophilic moieties of compounds of the invention permit their direct incorporation into lipid layers of lipososomes. Liposomes are advantageous in some conditions for intravenous administration due to improved efficacy and milder infusion reactions versus nonliposomal formulations. Liposomes are also suitable for inhalational delivery to treat fungal or parasitic infections of the lungs, or inflammation of the lungs and airways. In some embodiments, compounds of the invention are incorporated into liposomal delivery formulations with other drugs, including but not limited to antifungal agents such as liposomal amphotericin B, or anticancer agents such as liposomal doxorubicin. For treatment of inflammatory skin conditions or fungal infections of the skin or nails, or of nasal passages, compounds of the invention are applied topically in a pharmaceutically acceptable formulation. The topical composition can be in various forms, including, but not limited to, a solution, spray, gel, hydrogel, lotion, cream, ointment, paste, or an emulsion in the form of liquid suspension, lotion, or cream. The composition can also be applied via a dermal patch, Or bandage which can be applied on the affected area as needed, to provide an extended exposure of the skin to the medication; in such formulations, appropriate standard topical medicament excipients and vehicles are suitable for delivering compounds of the invention. Standard constituents for topical formulations are known in the art and are suitable as vehicles for compounds of the invention. Ointment bases can comprise one or more of hydrocarbons (paraffin wax, soft paraffin, microcrystalline wax, or ceresine), absorption bases (wool fat or beeswax), macrogols (polyethylene glycol), or vegetable oils. Lotions and creams are water in oil or oil in water emulsions; the oil components can comprise long chain fatty acids, alcohols or esters, and optional contain biocompatible nonionic surfactants. Compounds of the invention are incorporated into topical vehicles in concentrations ranging from 0.01% to 5%, preferably 0.02 to 1%. Compounds of the invention are applied to skin lesions once to three times per day for durations dependent on the rate of resolution of the condition.

For treatment of some lung infections, including fungal infections or parasites residing in alveolar macrophages, inhalational formulas of compounds of the invention are suitable. Excipients and inhalational drug delivery devices are known in the art and are useful for delivering compounds of the invention to treat lung infections, including cryptococcus and tuberculosis.

Compounds of the invention are advantageously coformulated with other antifungal or anti-inflammatory agents for topical or systemic administration, particularly when both drugs are appropriately administered via the same route and schedule. Compounds of the invention are compatible with standard formulations and excipients used for other topical or systemic antifungal or anti-inflammatory agents, including but not limited to ointments and tablets or capsules. Advantageous drug categories for combination in topical anti-inflammatory formulations include corticosteroids, calcineurin inhibitors and vitamin D analogues, and other agents known to have independent therapeutic activity in inflammatory skin conditions.

The invention will be better understood by reference to the following examples, which illustrate but do not limit the invention described herein.

CHEMICAL SYNTHESIS EXAMPLES

Example 1: Synthesis of 2-(3-Phenoxybenzyl)-1H-imidazo[4,5-c]quinoline

Step 1: 3-Nitroquinolin-4-ol

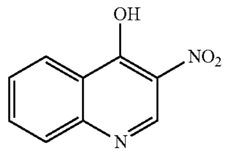 [SMILES: O=[N+]([O-])c1cnc2ccccc2c1O]

70% Aqueous nitric acid (6.1 mL) was added dropwise to a mixture of 4-hydroxyquinoline (10 g, 69 mmol) and 100 mL of acetic acid heated at reflux. After 15 min, the mixture was allowed to cool to room temperature. Dilution with EtOH resulted in the formation of a precipitate, which was filtered and washed sequentially with EtOH, $H_2O$, and EtOH. Drying of the filtrate in vacuo gave 4.62 g of a light yellow powder. $^1H$ NMR (400 MHz, DMSO-$d_6$) δ 9.2 (s, 1H), 8.3 (d, 1H), 7.9-7.7 (m, 2H), 7.5 (m, 1H).

Step 2: 4-Chloro-3-nitroquinoline

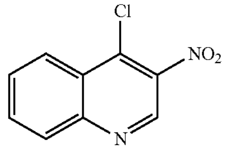 [SMILES: O=[N+]([O-])c1cnc2ccccc2c1Cl]

Phosphorus oxychloride (2.5 mL, 27 mmol) was added dropwise to a mixture of 3-nitroquinolin-4-ol (4.6 g, 24 mmol) and 100 mL of DMF. The mixture was heated at 100° C. for 15 min, and then poured onto stirred ice. The slurry was neutralized with solid $NaHCO_3$, and the precipitate was filtered and washed with saturated $NaHCO_3$ and $H_2O$. The filtrate was taken up in DCM, dried over anhydrous $Na_2SO_4$, and concentrated to give 2.3 g of solid.

Step 3: N-(tert-Butyl)-3-nitroquinolin-4-amine

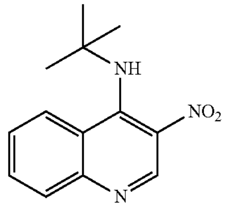 [SMILES: CC(C)(C)Nc1c([N+](=O)[O-])cnc2ccccc12]

A mixture of 4-chloro-3-nitroquinoline (6.30 g, 30.2 mmol), tert-butylamine (6.40 mL, 60.5 mmol), TEA (8.50 mL, 60.6 mmol), and 40 mL of DCM was heated at reflux for 5 hr., when the starting material was consumed. The mixture was stirred overnight at room temperature. The mixture was partitioned between DCM and saturated $NaHCO_3$, and the organic phase was dried over anhydrous $Na_2SO_4$ and concentrated to give the product.

Step 4: $N^4$-(tert-Butyl)quinoline-3,4-diamine

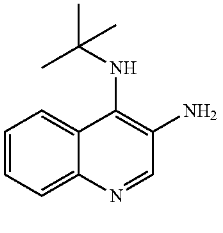 [SMILES: CC(C)(C)Nc1c(N)cnc2ccccc12]

N-(tert-Butyl)-3-nitroquinolin-4-amine obtained above, 10% Pd-C (630 mg), 1.5 mL of TEA, and 50 mL of MeOH were stirred under an atmosphere of hydrogen until the starting material was consumed. The hydrogen was replaced by nitrogen, and the mixture was filtered through a pad of Celite and concentrated. The residue was dissolved in 1:1:1 MeOH, DCM, and toluene spiked with 0.5 mL of TEA and then concentrated to give 7.37 g of material. Rf 0.50 (7.5% MeOH/DCM+1% TEA)

Step 5: N-(4-(tert-Butylamino)quinolin-3-yl)-2-(3-phenoxyphenyl)acetamide

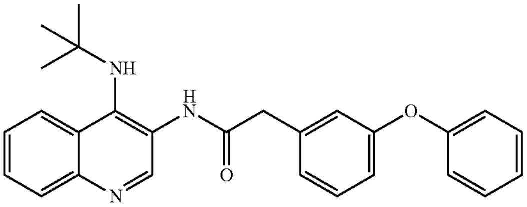 [SMILES: CC(C)(C)Nc1c(NC(=O)Cc2cccc(Oc3ccccc3)c2)cnc2ccccc12]

EDC (6.5 g, 33.8 mmol) was added to a mixture of $N^4$-(tert-butyl)quinoline-3,4-diamine (4.91 g, 22.2 mmol), 3-phenoxyphenylacetic acid (5.2 g, 22.8 mmol), HOBt (3.49 g, 22.8 mmol), and DMAP (0.60 g, 4.9 mmol) in 60 mL of 1:1 DMF/DCM. After 17.5 hr., TLC of an aliquot of the mixture showed unconsumed starting material, so additional EDC (2.12 g, 11.0 mmol) and DMF (15 mL) was added, and the mixture was warmed to 45° C. and the DCM was allowed to boil off. After 68 hr., the mixture was cooled and partitioned between EtOAc (3×250 mL) and 5% $Na_2CO_3$ (2×150 mL) and brine (150 mL). The organic phases were dried over anhydrous $Na_2SO_4$ and concentrated to give the product.

Step 6: N-(4-Aminoquinolin-3-yl)-2-(3-phenoxyphenyl)acetamide

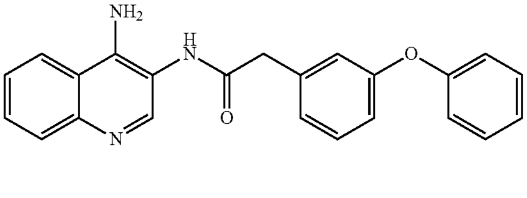 [SMILES: Nc1c(NC(=O)Cc2cccc(Oc3ccccc3)c2)cnc2ccccc12]

N-(4-(tert-Butylamino)quinolin-3-yl)-2-(3-phenoxyphenyl)acetamide was mixed with 1:1 TFA/DCM for 2 hr. at room temperature. The volatile components were evaporated, and the residue was dissolved in DCM and washed with 5% $Na_2CO_3$, and the organic phase was dried over anhydrous $Na_2SO_4$ and then concentrated. Purification by flash chromatography (5% MeOH/DCM+1% TEA) gave the product as a solid. The product was recrystallized from MeOH. LC-MS confirmed MW 369. Rf 0.25 (10% MeOH/DCM)

Step 7: 2-(3-Phenoxybenzyl)-1H-imidazo[4,5-c]quinoline

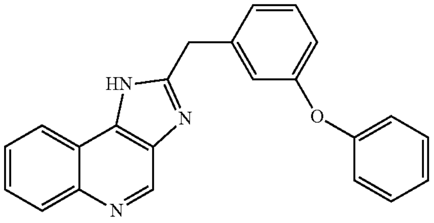 [SMILES: c1ccc(Oc2cccc(Cc3nc4cnc5ccccc5c4[nH]3)c2)cc1]

A mixture of N-(4-aminoquinolin-3-yl)-2-(3-phenoxyphenyl)acetamide (1.76 g, 4.77 mmol) and $NH_4Cl$ (21 mg, 0.39 mmol) in 25 mL of anisole was heated at reflux for 4.5 hr. The volatile material was evaporated, and the solid residue was partitioned between DCM and 5% $Na_2CO_3$. The organic phase was dried over anhydrous $Na_2SO_4$ and concentrated. Purification by flash chromatography (5% MeOH/DCM) gave 1.60 g of the product as a foamy solid. LC-MS confirmed MW 351. Rf 0.46 (10% MeOH/DCM); $^1H$ NMR (400 MHz, $CDCl_3$) δ 9.04 (br s, 1H), 8.25 (br s, 1H), 8.14 (d, 1H, J=8.7 Hz), 7.62-7.58 (m, 1H), 7.52 (br s, 1H), 7.27-7.22 (m, 3H), 7.18-7.14 (m, 1H), 7.08-7.04 (m, 1H), 6.97-6.95 (m, 1H), 6.90-6.86 (m, 3H), 6.81-6.79 (m, 1H), 4.34 (s, 2H)

BIOLOGICAL ACTIVITY EXAMPLES

Example A: Anti-Cancer Activity In Vitro

Compound AF has previously been identified as a potent lysosomotropic agent with anticancer activity against a number of cancer cell lines. The relative potency of Compounds GE and AF were compared in two cancer cell lines with very different genetic anomalies and oncogene drivers underlying for their tumorigenic properties.

PC3 (prostate cancer) and A549 (lung cancer) cell lines were cultured in medium consisting of 90% F-12K Nutrient Mixture (Kaighn's modification) with L-glutamine and 10% Hyclone Fetal Bovine Serum. No antibiotics were used in the medium.

PC3 and A549 cells were plated in 96 well plates at a density of 20,000 and 10,000 cells per well, respectively, in a volume of 0.1 ml per well. Twenty four hours after plating the cells, the medium was replaced with 0.1 ml of medium containing either the AF or the GE compounds. The AF compound was tested at concentrations of 1, 0.5, 0.25, and 0.1 micromolar. The GE compound was tested at concentrations of 0.1, 0.05, 0.025, and 0.01 micromolar. The cells were then cultured for 72 hrs, and cell viability was evaluated with the WST-1 assay at 48 and 72 hours.

For cell viability, the absorbance obtained in the WST-1 assay of cells exposed to the compounds was expressed as a percentage of the absorbance of wells of cells incubated in the absence of the compounds. All measurements are expressed as the average±SEM of 3 wells.

Figure 3:
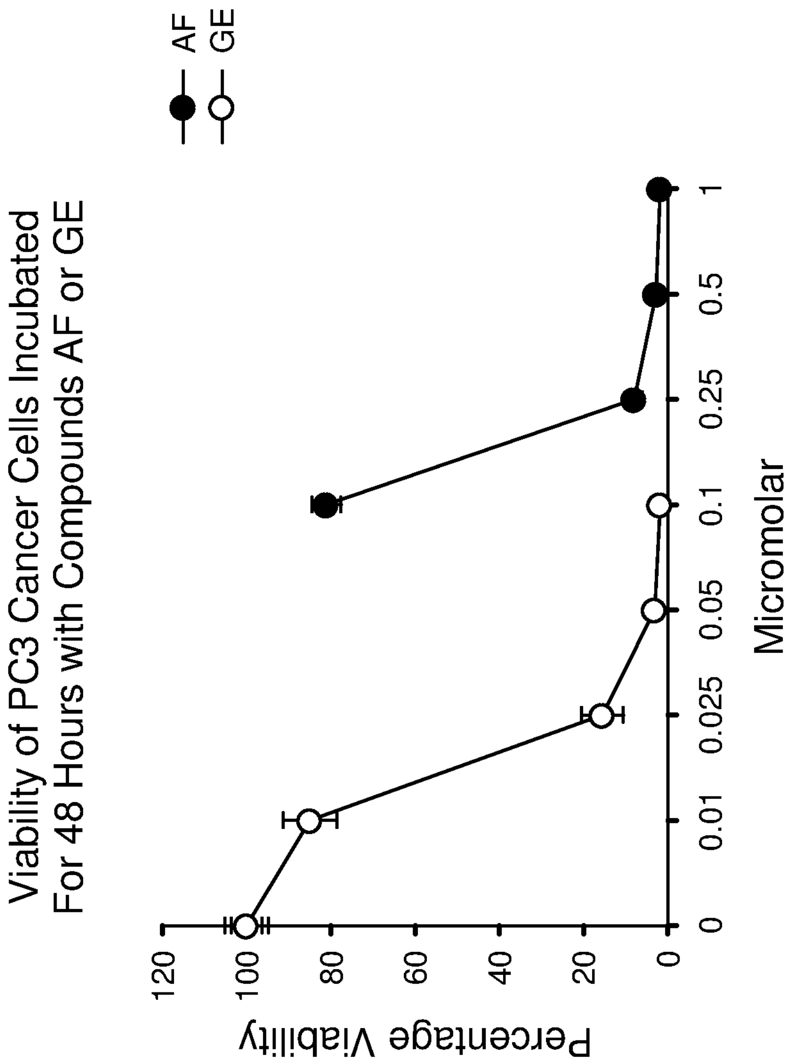
FIG. 3: Viability of PC3 Cancer Cells Incubated for 48 Hours with Compounds AF or GE
Figure 4:
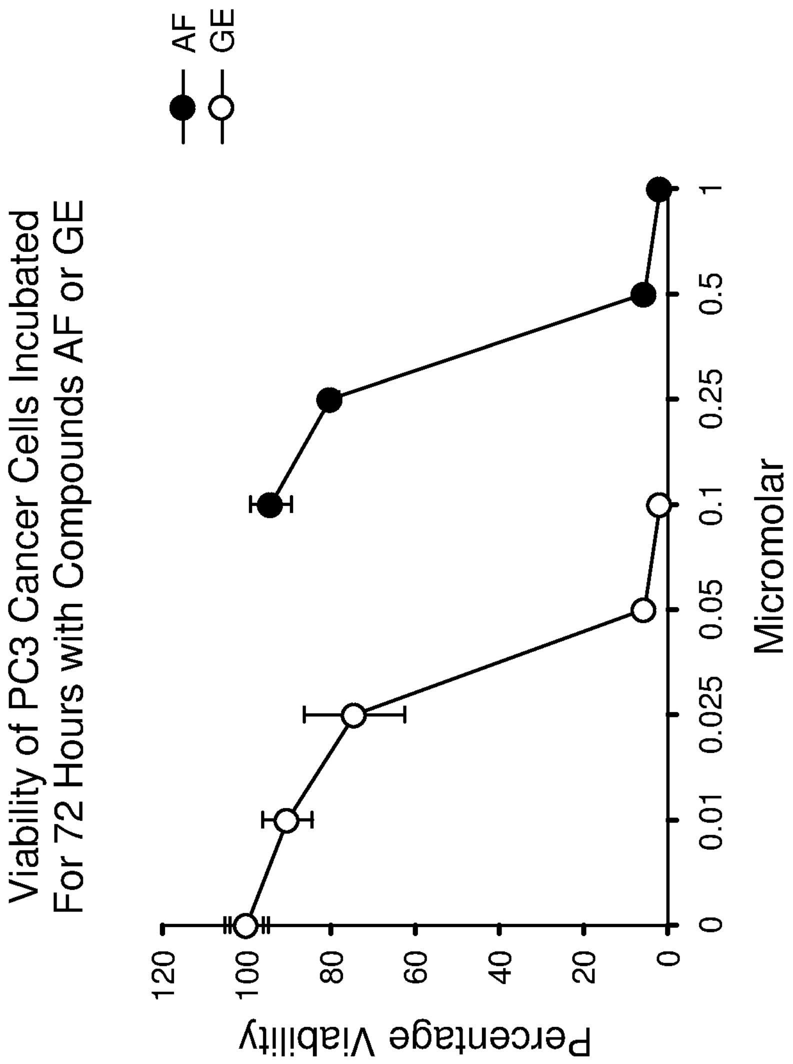
FIG. 4: Viability of PC3 Cancer Cells Incubated for 72 Hours with Compounds AF or GE

Cancer cell viability as a function of dose (concentration) of GE and AF is shown in FIGS. 1-4. Compound GE reduced viability of cancer cells at doses approximately 1/10 of those required for similar reductions in cell viability by compound AF in both A549 lung cancer cells (FIGS. 1 and 2) and in PC3 prostate cancer cells (FIGS. 3 and 4).

Example B. Anti-Inflammatory Effects of Compound GE on Psoriasiform Dermatitis in Mice Topical imiquimod (IMQ), a toll-like receptor agonist, has been established as a model of inflammatory skin diseases including psoriasis and atopic dermatitis that predicts clinical activity in human subjects. Dermal inflammatory changes and gene expression in mice treated with topical imiquimod mimic human psoriasiform dermatitis (van der Fits et al., 2009). The effect of Compound GE of the invention was tested in a mouse model of imiquimod-induced dermatitis.

Compound GE was dissolved in ethanol at a concentration of 0.1% and then mixed with 9 volumes of petrolatum (melted on a heated water bath at 50 degrees C.), yielding ointment containing 0.01% active drug. Petrolatum containing 10% ethanol was used as a control or vehicle treatment.

Female Balb/C mice weighing approximately 20 grams were randomized and divided into three groups of 5 animals each. Polyethylene collars were affixed to the mice to prevent them from easily scratching their ears.

5% imiquimod was applied to both ears of each mouse (20 microliters per ear) daily for 5 days, and then every other day for the full duration of the study Inflammatory changes, including an increase in ear thickness were apparent by day 5. On day 5 after initiation of imiquimod, treatment with Compound GE was started. Both ears of each mouse were treated with test ointments.

Ear thickness and PASI assessments (Psoriasis Area and Severity Index, a standard psoriasis scoring system capturing swelling, erythema and scaling) were recorded twice per week throughout the study.

Results

Figure 5:
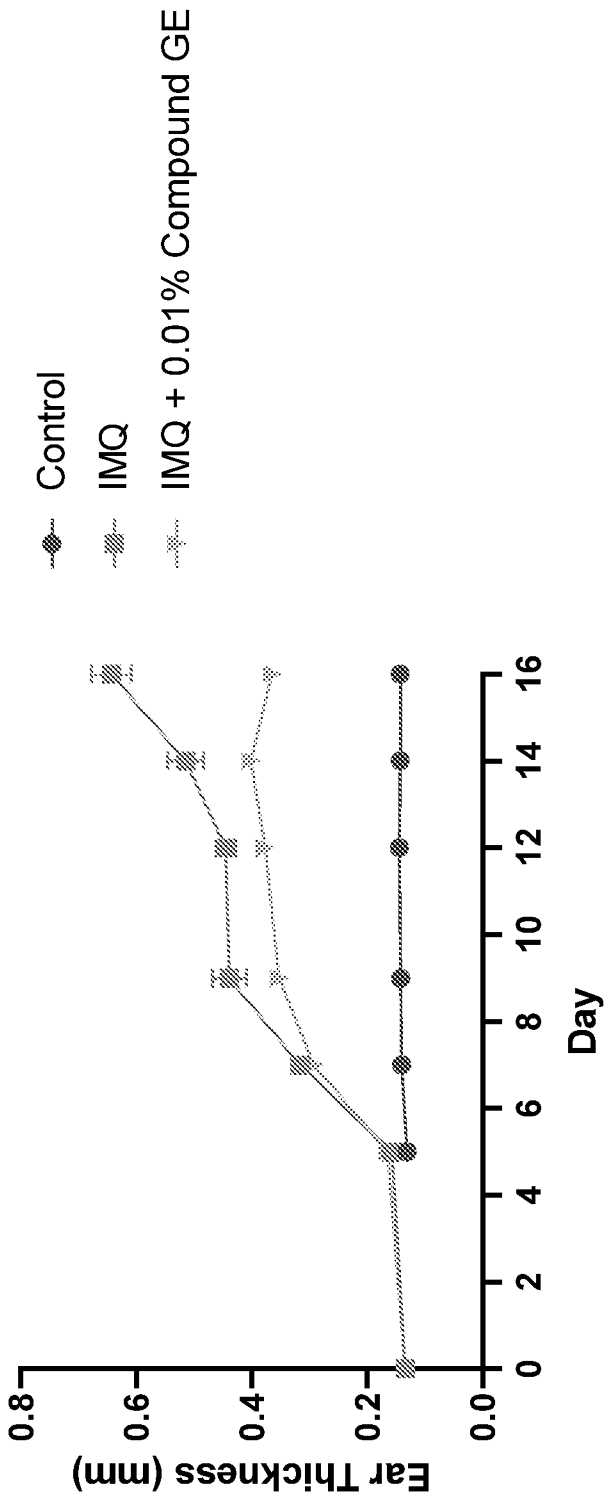
FIG. 5: Ear thickness in mice with imiquimod-induced dermatitis treated with Compound GE
Figure 6A:
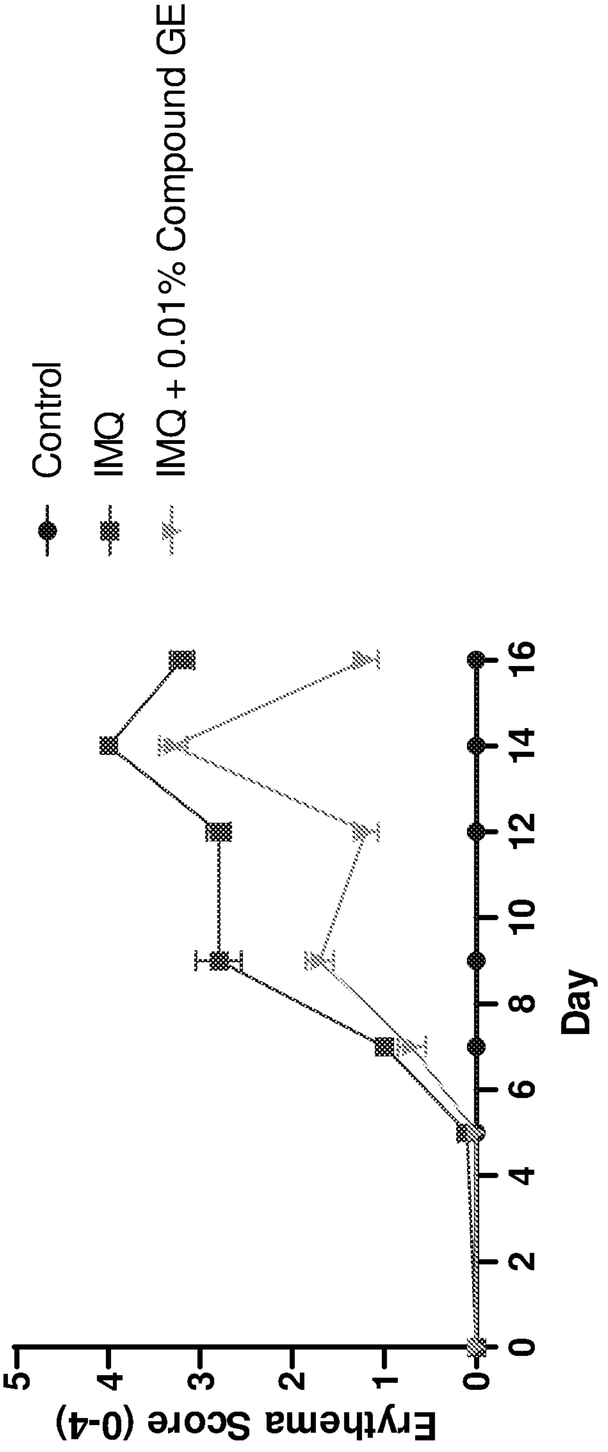
FIG. 6A: PASI Skin Erythema Score (0-4) in mice with imiquimod-induced psoriasiform dermatitis treated with Compound GE
Figure 6B:
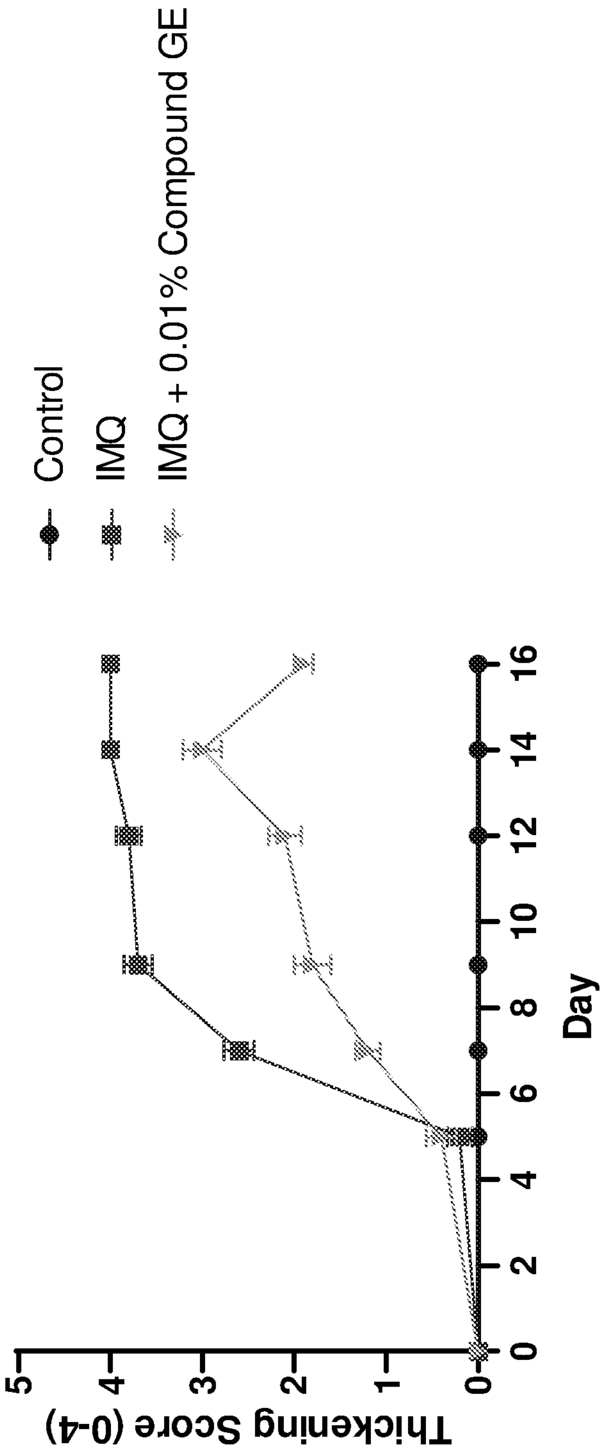
FIG. 6B: PASI Skin Thickening Score (0-4) in mice with imiquimod-induced psoriasiform dermatitis treated with Compound GE
Figure 6C:
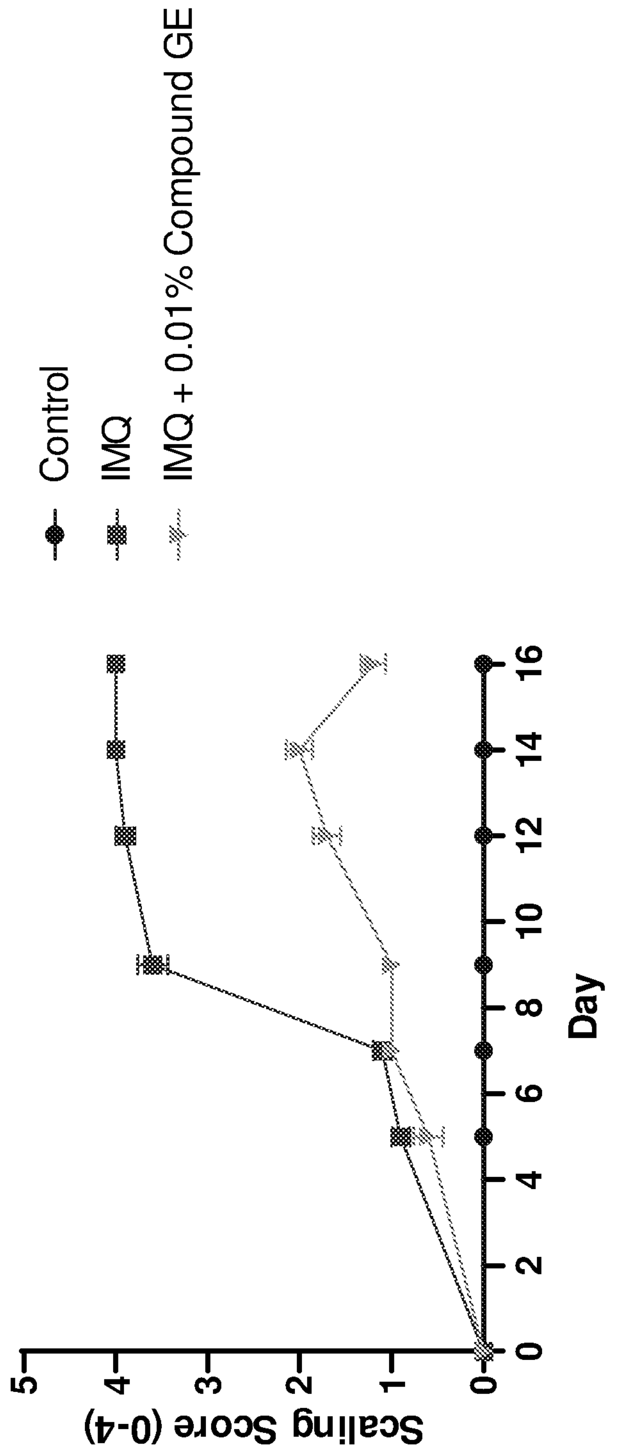
FIG. 6C: PASI Skin Scaling Score (0-4) in mice with imiquimod-induced psoriasiform dermatitis treated with Compound GE
Figure 6D:
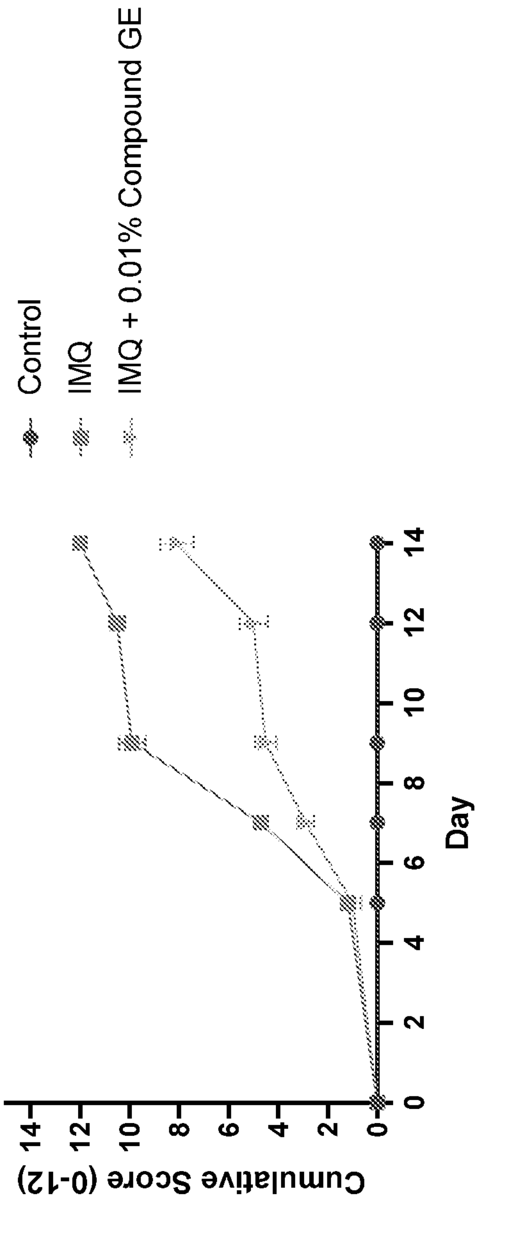
FIG. 6D: PASI Cumulative Score (0-12) in mice with imiquimod-induced psoriasiform dermatitis treated with Compound GE

Imiquimod treatment resulted in significant inflammatory changes, including an increase in ear thickness (FIG. 5) and a change in PASI scores; control ears reached the maximum possible value in the PASI (12, reflecting severe swelling, erythema and scaling, each with a scale of 0-4) scoring system (FIGS. 6A-D). Compound GE, applied topically in an ointment base, reduced imiquimod-induced inflammatory damage to mouse ears, as assessed by caliper measurements of thickness and PASI scoring of appearance, reducing all three aspects of dermal inflammation captured by the PASI scoring system. Compound GE was effective at a concentration of 0.01%, indicating high potency in this model of psoriasiform dermatitis.

REFERENCE van der Fits L, Mourits S, Voerman J S, Kant M, Boon L, Laman J D, Cornelissen F, Mus A M, Florencia E, Prens E P, Lubberts E. (2009) Imiquimod-induced psoriasis-like skin inflammation in mice is mediated via the IL-23/IL-17 axis. J Immunol. 182(9):5836-45.

What is claimed is:

1. A compound selected from the group consisting of:
2-(3-Phenoxybenzyl)-1H-imidazo[4,5-c]quinoline
and pharmaceutically acceptable salts thereof.

2. A method for treating a condition in a mammalian subject; the condition being selected from the group consisting of an inflammatory disease and a neoplastic disease; comprising administering to the subject an effective amount of the compound of claim 1.

3. The method of claim 2, wherein the mammalian subject is a human subject.

4. The method of claim 2, wherein the condition is an inflammatory disease, wherein the inflammatory disease is an inflammatory skin condition.

5. The method of claim 4, wherein the inflammatory skin condition is selected from the group consisting of psoriasis, psoriatic dermatitis, eczema, atopic dermatitis, and impetigo.

6. The method of claim 2, wherein the condition is an inflammatory disease, wherein the inflammatory disease is a systemic autoimmune disorder.

7. The method of claim 6, wherein the systemic autoimmune disorder is selected from the group consisting of rheumatoid arthritis, systemic and discoid lupus erythematosis, psoriatic arthritis, vasculitis, Sjogrens syndrome, scleroderma, autoimmune hepatitis, and multiple sclerosis.

8. The method of claim 2, wherein the condition is a neoplastic disease, wherein the neoplastic disease is a hematologic cancer or a solid tumor.

9. A composition comprising the compound of claim 1 and further comprising a pharmaceutically acceptable carrier.

10. The method of claim 2 wherein the compound is administered topically to the subject.

11. The method of claim 2 wherein the compound is administered systemically to the subject.

12. The method of claim 11, wherein the compound is administered orally, rectally, parenterally, or nasally.

* * * * *